United States Patent [19]
Stone

[11] Patent Number: 5,881,733
[45] Date of Patent: Mar. 16, 1999

[54] TECHNIQUE FOR OSTEOCARTILAGINOUS TRANSPLANTATION IN A MAMMALIAN JOINT

[75] Inventor: Kevin R. Stone, Mill Valley, Calif.

[73] Assignee: DePuy Orthopaedic Technology, Inc., Tracy, Calif.

[21] Appl. No.: 710,176

[22] Filed: Sep. 13, 1996

[51] Int. Cl.$^6$ .................................................. A61B 19/00
[52] U.S. Cl. ............................................ 128/898; 623/16
[58] Field of Search .................................. 128/897, 898, 128/754; 623/11, 16–17, 66, 18–22, 13, 14, 12

[56] References Cited

U.S. PATENT DOCUMENTS

| | | | |
|---|---|---|---|
| 4,642,120 | 2/1987 | Nevo et al. | 623/16 |
| 4,846,835 | 7/1989 | Grande | 623/11 |
| 4,895,146 | 1/1990 | Draenert | 128/754 X |
| 5,002,071 | 3/1991 | Harrell | 128/897 |
| 5,041,138 | 8/1991 | Vacanti et al. | 623/16 |
| 5,067,963 | 11/1991 | Khouri et al. | 623/16 |
| 5,067,964 | 11/1991 | Richmond et al. | 623/18 |
| 5,082,803 | 1/1992 | Sumita | 623/16 X |
| 5,092,887 | 3/1992 | Gendler | 623/13 |
| 5,281,422 | 1/1994 | Badylak et al. | 623/13 |
| 5,372,821 | 12/1994 | Badylak et al. | 623/13 X |
| 5,445,833 | 8/1995 | Badylak et al. | 623/11 X |
| 5,554,389 | 9/1996 | Badylak et al. | 424/558 |
| 5,556,429 | 9/1996 | Felt | 623/16 |
| 5,573,784 | 11/1996 | Badylak et al. | 24/551 |
| 5,612,028 | 3/1997 | Sackier et al. | 424/93.7 |
| 5,655,546 | 8/1997 | Halpern | 128/898 |

*Primary Examiner*—Mickey Yu
*Assistant Examiner*—Kelly O'Hara
*Attorney, Agent, or Firm*—Lappin & Kusmer LLP

[57] ABSTRACT

The invention disclosed is a method for repairing focal arthritic defects in a mammalian joint, especially in a human knee. The method involves the steps of forming a roughened, bleeding surface of cancellous bone within the defect; forming a plug of osteocartilaginous tissue from an undamaged site within the joint or from another joint; removing the plug from the undamaged site; and inserting the plug into the defect, positioning the plug against the roughened bleeding surface, and holding the plug in place for a time sufficient to allow a blood clot to form between the plug and the roughened bleeding surface, whereby the plug is secured by adhesive properties of the clot.

11 Claims, No Drawings

TECHNIQUE FOR OSTEOCARTILAGINOUS TRANSPLANTATION IN A MAMMALIAN JOINT

The present invention relates to the field of surgical methods for treatment of a focal arthritic defect in a joint of a mammal, and more particularly, for treatment of focal arthritic defects in the knee of a mammal.

BACKGROUND OF THE INVENTION

Focal arthritic defects are defined as areas of complete hyaline cartilage loss exposing the underlying bone ringed by areas of intact hyaline cartilage. Focal arthritic defects may occur as the result of trauma or other conditions, such as loss of the protective meniscus cartilage or osteoarthritis. Focal arthritic defects may occur in any joint, being especially problematic in the weight-bearing joints, i.e., in the hip, the knee, and the ankle. Focal arthritic defects in these joints lead to pain, swelling, and loss of motion. In the past, treatment of focal arthritic defects has included drilling, abrasion, periosteal covering and bone grafting.

SUMMARY OF THE INVENTION

The present invention provides a surgical technique in which an osteocartilaginous plug, or graft, can be removed from one location within a mammalian joint and moved to another location within the joint, or to another joint, to fill a focal arthritic defect In one embodiment, the invention provides a method of repairing an arthritic defect in a mammalian joint which comprises the steps of forming a roughened, bleeding surface of cancellous bone within the defect; forming a plug of osteocartilaginous tissue from an undamaged site within the joint or from another joint; removing said plug from said undamaged site; and inserting the plug into the defect, positioning said plug against the roughened bleeding surface, and holding the plug in place for a time sufficient to allow a blood clot to form between said plug and said roughened bleeding surface.

DESCRIPTION OF THE PREFERRED EMBODIMENT

The method of the invention is suitable for repairing any arthritic defect in any joint, so long as the defect is not so extensive that no undamaged portion of the joint remains. Preferably, the method of the invention is used to repair focal arthritic defects in the hip. More preferably, the method of the invention is used to repair focal arthritic defects in the ankle. Most preferably, the method of the invention is used to repair focal arthritic defects in the knee. Focal arthritic defects in the joints of any mammal may be repaired in accordance with the method of the invention. Preferably, focal arthritic defects in the joints of humans may be repaired using the method of the invention.

For example, when the joint being repaired is a knee, after routine arthroscopic examination has been performed and a focal arthritic defect has been identified, the procedure is performed as follows.

The base of the arthritic defect where the exposed bone is visualized, is prepared by fracturing at a predetermined depth and a plurality of locations with elongated pointed objects, such as arthroscopic awls similar to ice picks to form a prepared bed. Preferably, the fracture holes are approximately 5–10 mm deep, with an inter-hole spacing in the range 1–5 mm, and most preferably 2–3 mm. Fracturing of the base produces bleeding. The blood forms clots over the roughened cancellous bone exposed by the fracturing. Attention is next turned to the intercondylar notch between the two femoral condyles. Within the notch lies the anterior and posterior cruciate ligaments. The area anterior to the anterior cruciate ligament on the medial wall of the lateral femoral condyle is exposed with a curette, removing overlying soft tissue. A metal trephine coring device is then manually bored into the osteocartilaginous surface and down into the underlying cancellous bone to establish an osteocartilaginous graft. Preferably, the graft has a thickness in the range 1–2 cm. The bore is then backed out of the knee joint and then pointed at the prepared bed of the arthritic defect. The core of osteocartilaginous tissue, i.e., the graft, is then pushed into the defect with the plunger and held in place for a time sufficient to allow a blood clot to form between the graft and the roughened bleeding surface, such as for three minutes. As blood clots, the graft is secured by the adhesive properties of the clot. The instruments are then removed and the patient kept non weight-bearing for four weeks.

In one form of the invention, prior to insertion, the osteocartilaginous graft may be exposed to a proteinaceous factor which stimulates the formation of cartilage. Any cartilage-stimulating factor may be used in this embodiment, so long as the factor is capable of increasing the amount or rate of formation of cartilaginous tissue within a joint For example, the graft may be exposed to a cartilage-stimulating factor belonging to the transforming growth factor-$\beta$ (TGF-$\beta$) supergene family. Such a cartilage-stimulating factor may be in homodimeric or heterodimeric form. The cartilage-stimulating factor may be purified from mammalian tissue or it may produced recombinantly from one or more cDNAs encoding a monomer of the cartilage-stimulating factor. The graft is exposed to a therapeutically effective amount of the cartilage-stimulating factor. As used herein, a "therapeutically effective amount" means the total amount of cartilage-stimulating factor sufficient to show a meaningful patient benefit, i.e., to enhance formation of cartilage in the vicinity of the graft.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

What is claimed is:

1. A method of repairing an arthritic defect in a mammalian joint which comprises the steps of:
   A. forming a roughened bleeding surface of cancellous bone within the defect;
   B. forming a plug of osteocartilaginous tissue from an undamaged site within the joint or another joint;
   C. removing said plug from said undamaged site; and
   D. inserting said plug into the defect, positioning said plug against said roughened bleeding surface, and holding said plug in place for a time sufficient to allow a blood clot to form between said plug and said roughened bleeding surface, whereby said plug is secured by adhesive properties of said clot.

2. The method of claim 1, wherein the joint is a knee joint.

3. The method of claim 2, wherein said undamaged site is an intercondylar notch.

4. The method of claim 1, wherein step A further comprises a step of fracturing a surface of the defect.

5. The method of claim 4 wherein said fracturing step includes the substep of driving an elongated pointed object into said surface to a predetermined depth and at a plurality of locations.

6. The method of claim 5 wherein said depth is in the range of 5–10 mm.

7. The method of claim 6 wherein the locations are spaced apart in the range of 1–5 mm.

8. The method of claim 6 wherein the locations are spaced apart in the range of 2–3 mm.

9. The method of claim 5 wherein the locations are spaced apart in the range of 1–5 mm.

10. The method of claim 5 wherein the locations are spaced apart in the range of 2–3 mm.

11. The method of claim 1 wherein said forming step B includes the substep of:

applying a coring device to said undamaged site to form said plug, whereby said plug has a depth in the range of 1–2 cm.

* * * * *